(12) United States Patent
Smith

(10) Patent No.: US 11,905,508 B2
(45) Date of Patent: Feb. 20, 2024

(54) CELL HARVESTING AND ISOLATION

(71) Applicant: Global Life Sciences Solutions USA LLC, Marlborough, MA (US)

(72) Inventor: Trevor Smith, Marlborough, MA (US)

(73) Assignee: Global Life Sciences Solutions USA LLC, Marlborough, MA (US)

(*) Notice: Subject to any disclaimer, the term of this patent is extended or adjusted under 35 U.S.C. 154(b) by 466 days.

(21) Appl. No.: 16/955,194

(22) PCT Filed: Dec. 14, 2018

(86) PCT No.: PCT/EP2018/085065
§ 371 (c)(1),
(2) Date: Jun. 18, 2020

(87) PCT Pub. No.: WO2019/121423
PCT Pub. Date: Jun. 27, 2019

(65) Prior Publication Data
US 2020/0332247 A1    Oct. 22, 2020

Related U.S. Application Data

(60) Provisional application No. 62/608,117, filed on Dec. 20, 2017.

(51) Int. Cl.
| C12M 1/00 | (2006.01) |
| C12M 1/12 | (2006.01) |
| C12M 1/26 | (2006.01) |
| C12M 1/42 | (2006.01) |

(52) U.S. Cl.
CPC ............ *C12M 47/04* (2013.01); *C12M 25/16* (2013.01); *C12M 33/14* (2013.01); *C12M 35/06* (2013.01)

(58) Field of Classification Search
CPC ...... C12M 25/16; C12M 33/14; C12M 35/06; C12M 47/04
See application file for complete search history.

(56) References Cited

U.S. PATENT DOCUMENTS

| 2008/0038807 | A1 | 2/2008 | Pommersheim | |
| 2010/0291219 | A1 | 11/2010 | Karp et al. | |
| 2013/0210130 | A1 | 8/2013 | Larcher et al. | |
| 2016/0312168 | A1* | 10/2016 | Pizzi | C12M 47/10 |
| 2017/0315121 | A1* | 11/2017 | Wegener | A61M 1/362 |
| 2019/0212233 | A1* | 7/2019 | Jovanovich | G01N 35/00 |

FOREIGN PATENT DOCUMENTS

EP     3238760 A1    11/2017

OTHER PUBLICATIONS

PCT International Search Report and Written Opinion for PCT Application No. PCT/EP2018/085065 dated Apr. 12, 2019 (11 pages).
Database WPI, Week 200630, Thomson Scientific, London, GB; AN 2006-293763, XP002790304, & WO 2006/038405 AI (Japan Sci&Technology Agency) Apr. 13, 2006 (Apr. 13, 2006) abstract.

* cited by examiner

*Primary Examiner* — Christine T Mui
*Assistant Examiner* — Kathryn Elizabeth Limbaugh
(74) *Attorney, Agent, or Firm* — Eversheds Sutherland (US) LLP

(57) ABSTRACT

This present invention provides means for cell harvesting and isolation to be carried out with a single apparatus. This represents a more convenient way for the processing of cells compared with known methods and represents a useful development for the manufacture of cell therapies.

23 Claims, 9 Drawing Sheets

CELL HARVESTING AND ISOLATION

CROSS REFERENCE TO RELATED APPLICATIONS

This application claims the priority benefit of PCT/EP2018/085065 filed on Dec. 14, 2018, which claims priority benefit of U.S. Provisional Patent Application No. 62/608,117 filed on Dec. 20, 2017, the entire contents of which are hereby incorporated by reference herein.

TECHNICAL FIELD OF THE INVENTION

This invention relates to an apparatus that can carry out both cell harvesting and isolation and to a method of use thereof.

DESCRIPTION OF RELATED ART

Cell therapy has long sat at the cusp of curative medicine, yet the clinical potential has not yet been realized. A major obstacle is the complexity in the manufacture of cell therapies due to the requirement for collection and processing of intact living cells. Careful consideration needs to be given to the science, product quality, patient safety, and regulation of all processes. Also, finding and optimizing the best technology for manufacture has been a complicating factor for researchers. There is a lack of standardization in manufacture, which makes it difficult to scale-up therapies to deliver to the hundreds of thousands of patients that could benefit. Even taking the upstream part of the manufacturing process alone, there are multiple methods and systems available for each of the steps of cell isolation, expansion and harvesting. Separate instrumentation and techniques are typically used for each step. It would be beneficial to have a complete ecosystem of tools which form a start to finish solution for cell therapy manufacture.

SUMMARY OF THE INVENTION

In one aspect, the present invention relates to a system for harvesting and isolating cells from a mixed cell suspension wherein said system comprises a housing for accommodating the following elements:
   at least one fluid pump;
   at least one valve; and,
   a magnet (9);
   the system further comprising a fluidic arrangement including:
   a fluid processing reservoir (7);
   a filter (8) suitable for separating cells from suspension fluid; and,
   plural sealed fluid paths (5), wherein at least portions of the fluid paths comprise flexible tubes (6) providing fluid communication at least between the filter and the reservoir, the outer surfaces of which are manipulatable by the or each fluid pump (3), to provide fluid flow in one or more of the paths (5) and/or by the or each valve (4) to restrict fluid flow in one or more of the paths (5);
   and said magnet (9) arranged to selectively engage with said filter (8) when the filter (8) is inserted into the housing.

In another aspect, the present invention relates to a method to isolate a desired cell type from a mixed cell suspension wherein said method comprises the following sequential steps:
   a. providing the system of the invention;
   b. inserting and connecting the elements of the system;
   c. adding said mixed cell suspension to said fluid processing reservoir;
   d. adding magnetic cell capture beads to said fluid processing reservoir wherein said magnetic capture beads selectively bind either to a specific undesired cell type or to a specific desired cell type;
   e. engaging the magnet with said filter to either trap said undesired cell type and allow said desired cell type to return to said fluid processing reservoir or to trap said desired cell type in said filter and allow said undesired cell type to flush to waste.

BRIEF DESCRIPTION OF THE FIGURES

FIG. 2 the magnet engaged with the filter.

FIG. 3 the magnetic cell capture beads being added to the fluid processing reservoir.

FIG. 4 shows activation of the magnet around the filter to capture the beads.

DETAILED DESCRIPTION OF THE PREFERRED EMBODIMENTS

Figure 1:
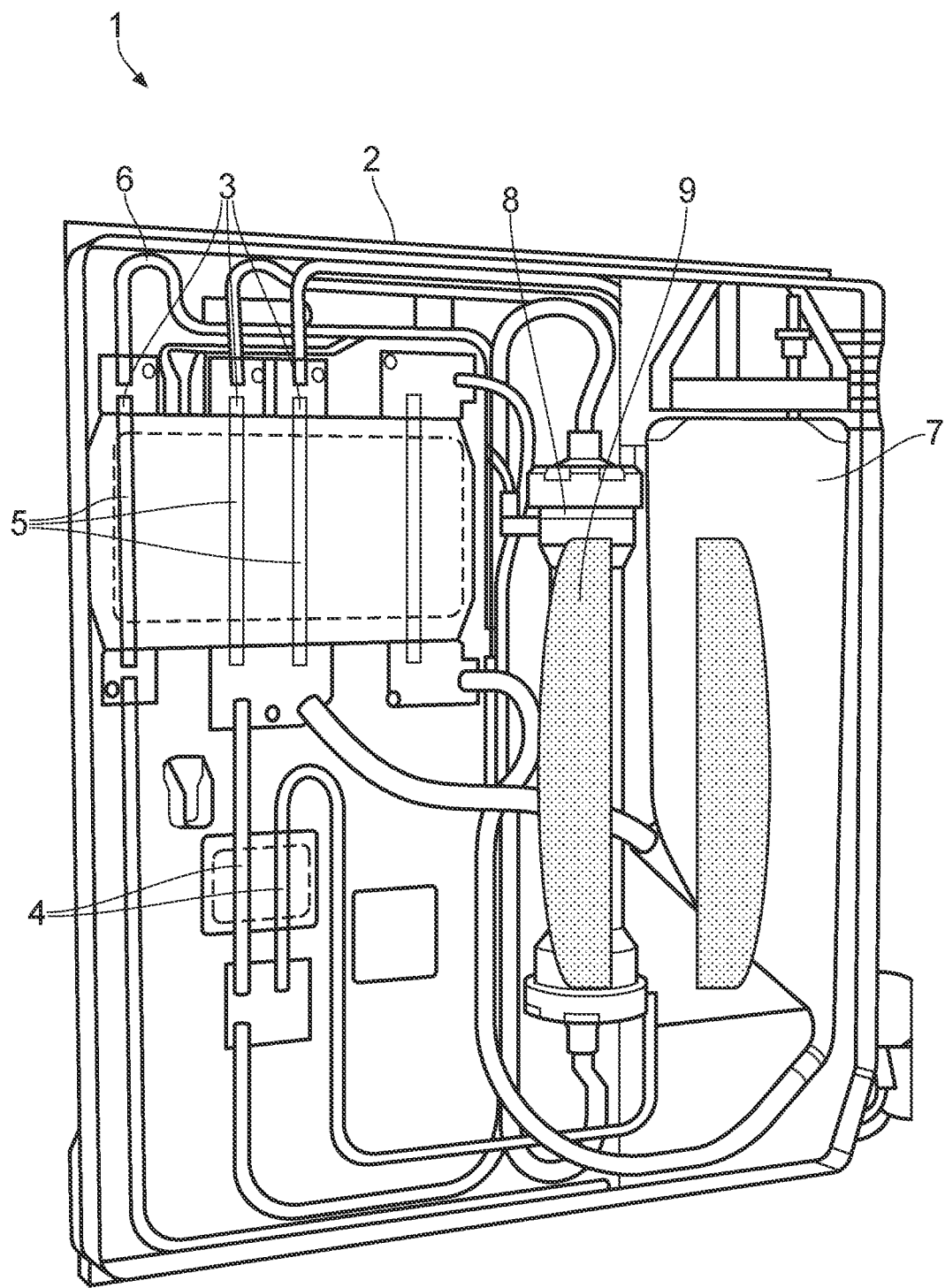
FIGS. 1-4 illustrate an embodiment of the system of the invention showing an embodiment of how it is put to use. The magnet in a retracted position is shown in FIG. 1.
Figure 2:
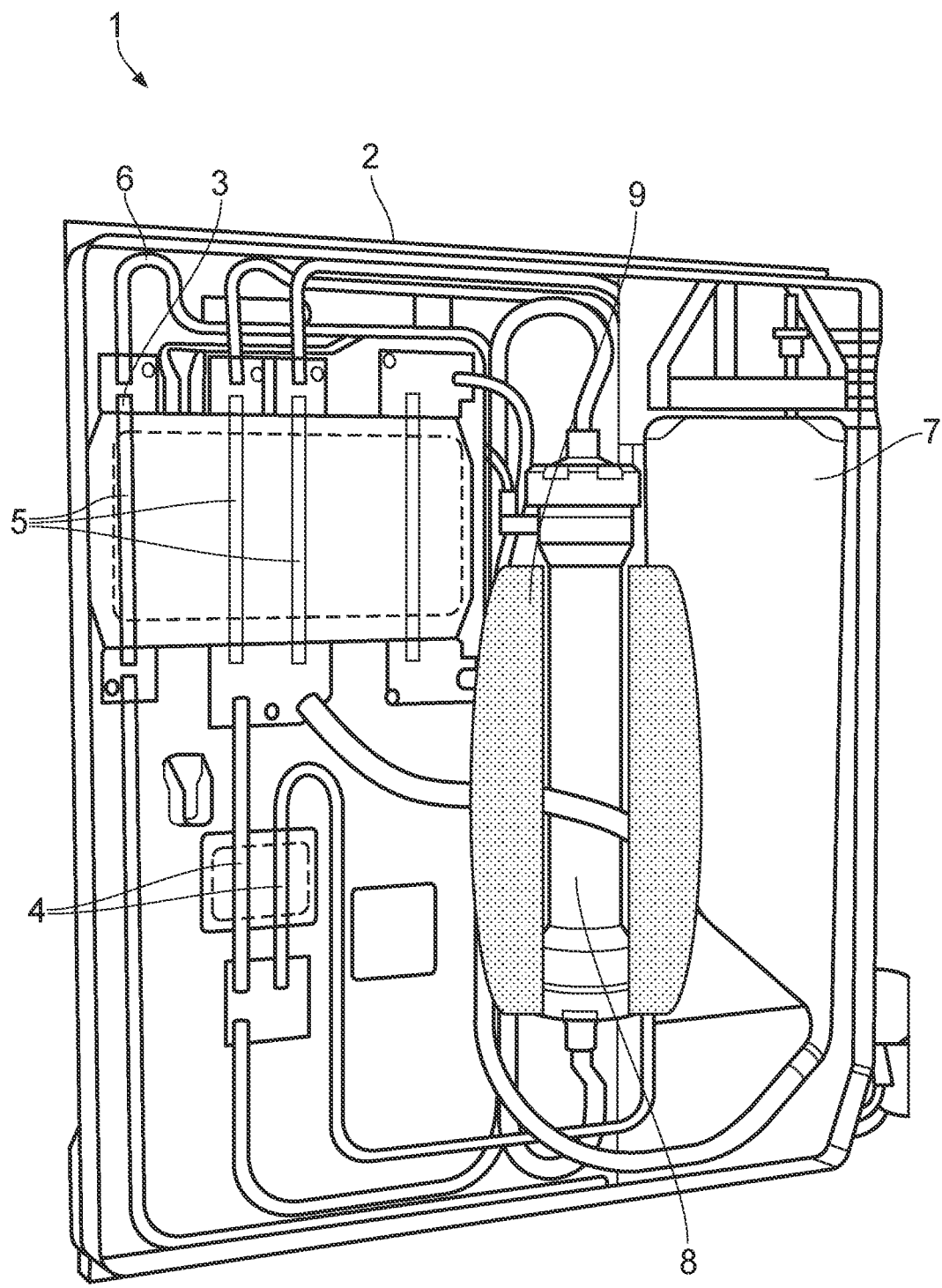
Figure 3:
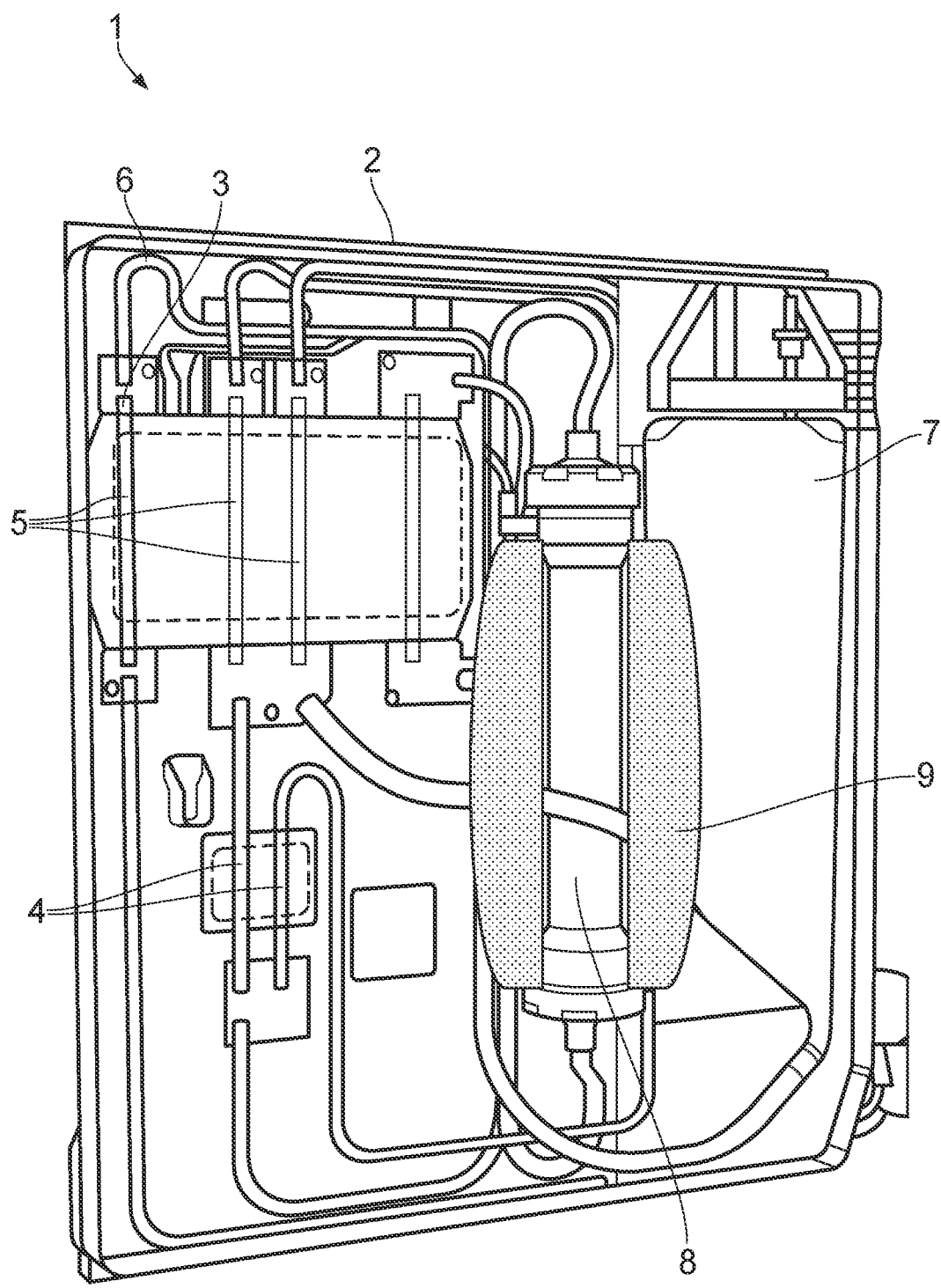
Figure 4:
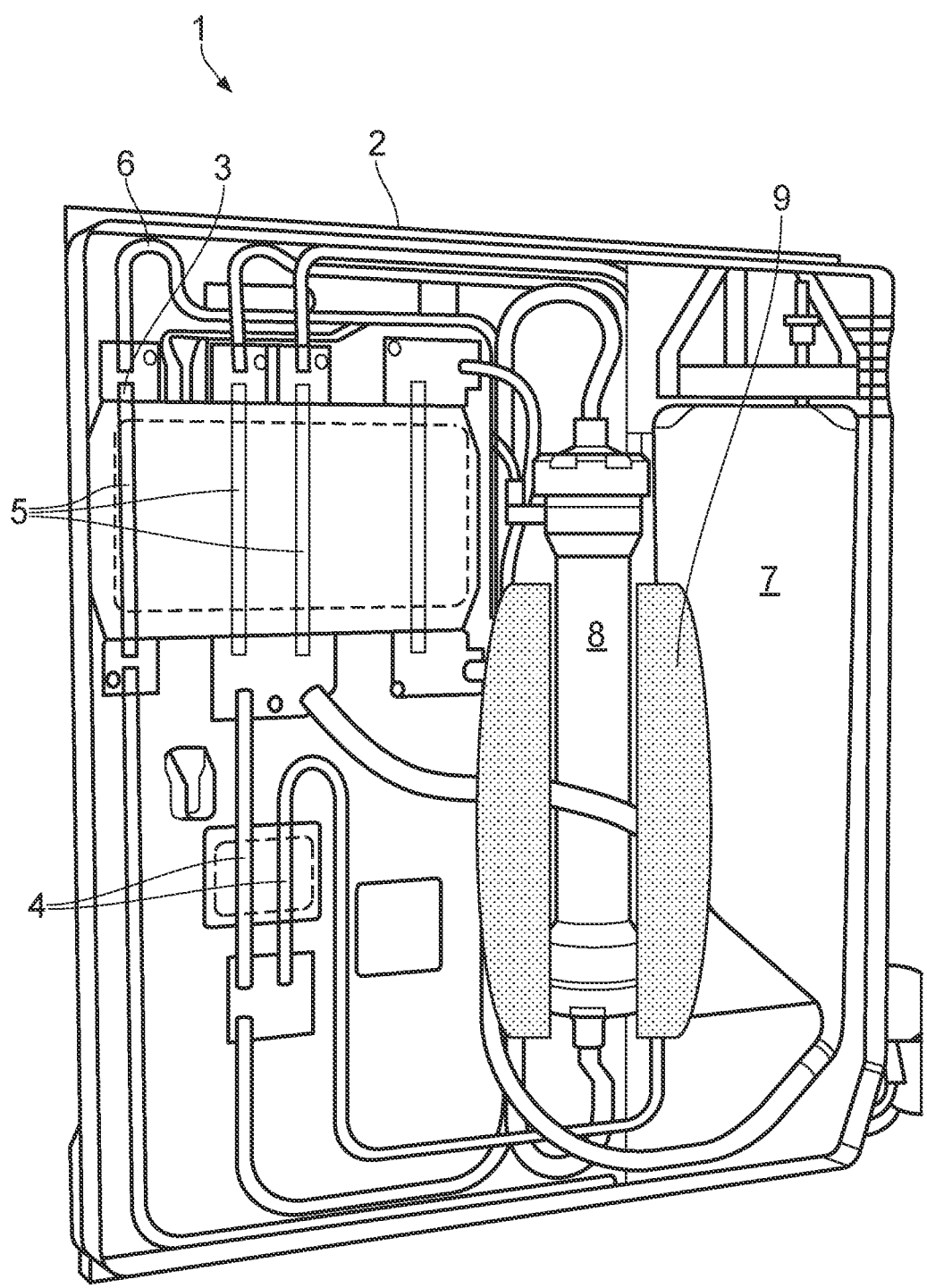
Figure 5:
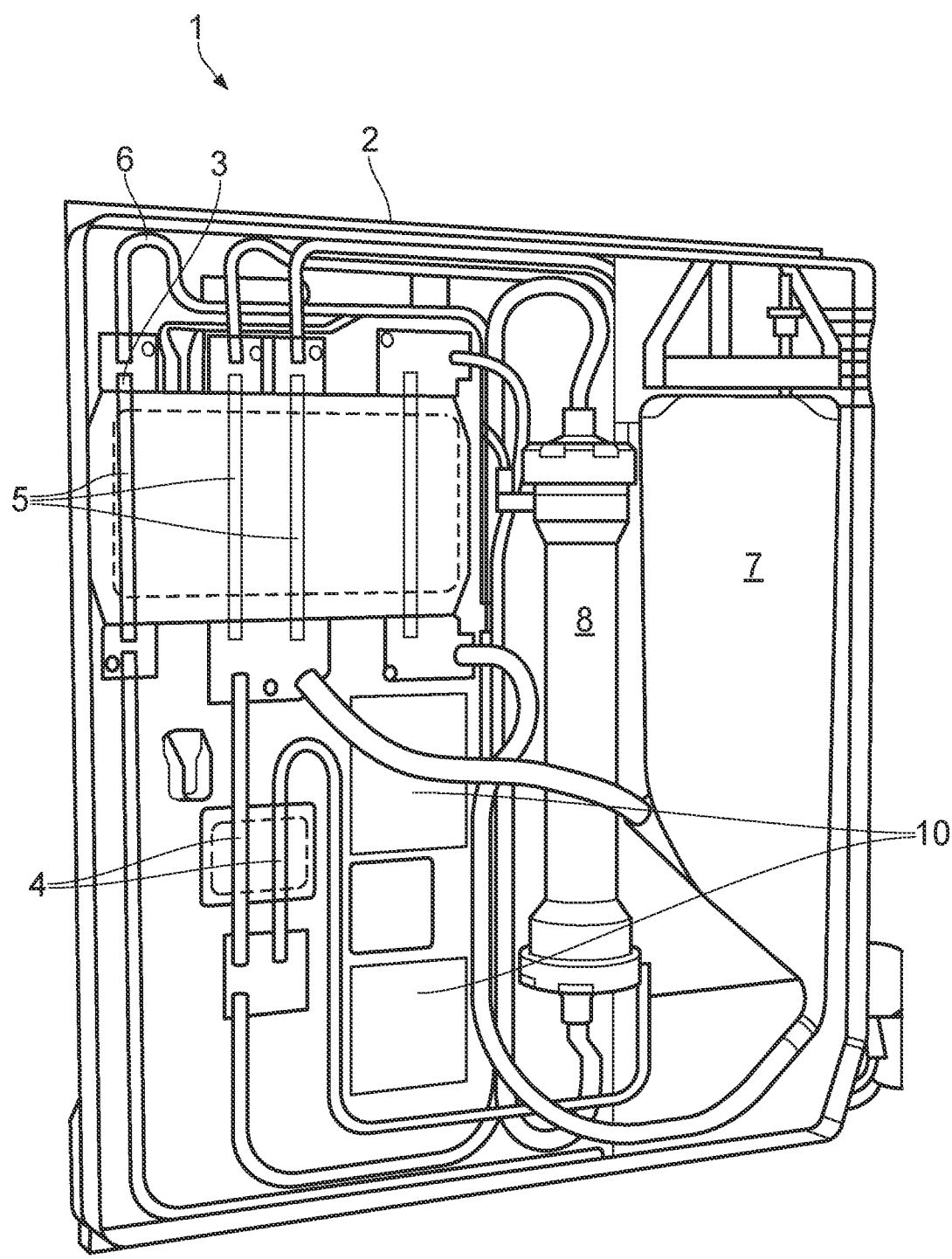
FIG. 5 shows an embodiment of the invention including placement for selection components.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "harvesting" refers to the processes used to concentrate a cell suspension, typically followed by one or more wash cycles to ensure high quality product.

The term "isolating" refers to the processes used to separate a desired cell type or types from a mixed cell suspension.

The term "mixed cell suspension" encompasses any fluid in which a heterogenous population of intact cells is suspended, including those which are naturally-occurring such as circulating blood and umbilical cord blood, derivatives thereof such as bone marrow suspensions, and artificially-created mixed cell suspensions such as a liquid cell culture.

The term "housing" refers to the casing that encloses and protects the functional elements of the system of the invention, and is preferably a rigid casing.

A "fluid pump" in the context of the present invention is any device that can move a fluid contained in a sealed fluid path by mechanical action. Suitably the fluid pump of the present invention is a positive displacement pump, e.g. a peristaltic pump.

A "valve" can be understood as any suitable device for controlling the passage of fluid through the sealed fluid paths of the invention. One example that can be used is a pinch type valve.

The "sealed fluid paths" of the system of the invention are fluid-tight conduits that serve to transfer fluid (i.e. the mixed cell suspension being processed or any reagents being used in its processing) into and out of the fluid processing reservoir and/or the filter.

The term "flexible tubes" refers to parts of the fluid paths made from a material able to recoil or spring back into shape after bending, stretching, or being compressed. Suitable materials include certain polymers and plastics, non-limiting examples of which include PVC and silicone.

The "fluid processing reservoir" is a fluid holding chamber suitable for containing the mixed cell suspension while maintaining cell quality. A typical fluid processing reservoir is made from moulded plastic, a non-limiting example of which is styrene butadiene copolymer.

A "filter" can be understood to be any a porous device for removing impurities or solid particles from a liquid or gas passed through it. In one embodiment of the present invention the filter is a hollow fibre filter.

A "magnet" in the context of the present invention acts as a magnet when an electric current passes through it but stops being a magnet when the current stops. The magnet of the invention needs to be configured to fit within the housing and be selectively engageable with the filter.

The term "selectively engage" means that in one configuration the magnet is physically removed from around the filter and in another configuration engages with the filter such that the contents of the filter are subjected to a magnetic field.

The term "processing kit" refers to a pre-assembled, single-use article that includes one or more of said sealed fluid paths, said fluid processing reservoir and said filter. The processing kit is suitably provided in sterile form.

The term "generally flat plane" refers to the configuration of the processing kit being compact and compatible with insertion into said housing and facile connection following insertion.

The term "motorized arm" refers to any suitable actuator that can fit within the housing and that is connected to said magnet so as to permit selective engagement of the magnet with said filter.

The "weighing mechanism" permits the volume of liquids in the reservoir to be estimated in use and typically comprises a hook within the housing operably connected to a weighing scales. In one embodiment there is a transfer mechanism housed within the housing for transferring the fluid processing reservoir onto said hook so that the volume of liquids in the reservoir can be estimated in use. In certain embodiments, the mechanism removes the reservoir from the processing kit support frame, transfers it to hook, which is supported by a load cell where it will stay for the duration of a processing run, and then returns the reservoir to the support frame.

The term "retracted position" refers to the position of the pumps and valves to allow the processing kit to be inserted and connected within the housing. The pumps and valves are brought into a position ready to operate (i.e. "operative position") by pivoting forward the pump assembly once the processing kit is in place.

The "guide rails" are supported within the housing, e.g. by a rigid device frame and are designed to slidably support and locate the processing kit. In one embodiment there are "complementary guiding formations" on the kit helping to ensure that the kit and pump heads are aligned more accurately than relying on the guide rails alone.

The "internal frame" comprises fixing mechanisms on the inside surface of the housing suitable for supporting the functional elements of the system.

The "reaction faces" are faces that are moulded to mate against either the pump head or the pinch valves when they engage with the fluid paths.

The term "magnetic cell capture beads" refers to small coated magnetised particles or beads. Typical magnetic cell capture beads consist of a core, e.g. an iron-containing core, covered by a thin layer of a polymer shell allowing the absorption of biomolecules. The beads are coated with antibodies, lectins, enzymes, or streptavidin. The beads bind to specific biomolecules on desired or undesired cells in the mixed cell suspension, which can then be gently separated by application of a magnetic field. Typically multiple cycles of washing follow in order to obtain the desired cell population. Non-limiting examples of suitable magnetic beads include the commercially-available DYNABEADS (Thermo Fisher) and SERAMAG (GE Healthcare Life Sciences).

A "cell lysis buffer" is a buffer solution used for the purpose of breaking open cells. A typical lysis buffer contains salts (e.g. Tris-HCl or EDTA) to regulate the acidity and osmolarity of the lysate. Sometimes detergents (such as Triton X-100 or SDS) are added to break up membrane structures. In one embodiment the cell lysis buffer is a red blood cell lysis buffer, the typical components of which are ammonium chloride, sodium bicarbonate, EDTA, and water.

The terms "undesired cell" and "desired cell" as used herein refer to cells that are eliminated or retained, respectively, from the mixed cell suspension. In one non-limiting example, CD3+ cells from whole blood can be regarded as a desired cell, with RBC's, platelets, and CD3− cell types being undesired cell types.

The term "expelled" refers to passing particular components out of the system. In one non-limiting example, the mixed cell suspension is whole blood and the filter is a hollow fibre filter. Following treatment of the whole blood with RBC lysis buffer, the components to be expelled include contaminating factors such as platelets and plasma, and the cellular debris generated from the RBC lysis. Each fibre of the hollow fibre filter cartridge is a long tube with multiple pores along its length. When whole blood that has been treated with RBC lysis buffer is passed through the cartridge, cellular debris from RBCs will get lodged in these pores and into the waste, while the target cells will remain in the fluid path.

In one embodiment of the system of the present invention said at least one fluid pump, said at least one valve and said magnet are present in said system.

In one embodiment of the system of the present invention one or more of said sealed fluid paths, said fluid processing reservoir and said filter are provided as a processing kit removably insertable into the housing.

In one embodiment of the system of the present invention said fluid paths in said kit are arranged in a generally flat plane.

In one embodiment of the system of the present invention at least one of said fluid paths is provided separately to said kit and fluidly connected to said fluid processing reservoir via selection component slots.

In one embodiment of the system of the present invention said magnet is present in said system on a motorized arm.

In one embodiment of the system of the present invention said filter is a hollow fibre filter.

In one embodiment the system of the present invention further comprises a weighing mechanism operable to weigh said fluid processing reservoir in use.

In one embodiment of the system of the present invention said pump(s) or said valve(s), in a retracted position, allow insertion and removal of the processing kit, and are driven into an operative position once the kit is inserted into the housing.

In one embodiment of the system of the present invention the housing includes a pair of guide rails to guide the kit into the housing during said insertion said guide rails and said kit having complementary guiding formations including a stop feature. In one embodiment the guide rails are supported on an internal frame, and the internal frame supports also the remaining elements.

In one embodiment of the system of the present invention each pump includes a peristaltic type pump head and the or each valve is a pinch type valve including pinch fingers, and the internal frame further supports reaction faces for reacting the forces exerted by the pump head(s) and by the valve fingers.

In one embodiment of the system of the present invention said kit frame comprises one or more through-apertures allowing the pump head(s) and pinch valve finger(s) to access the flexible tubes from one side of the frame and allowing the reaction faces to access the flexible tubes on the opposing side of the frame.

In one embodiment of the system of the present invention one of said sealed fluid paths is for the selective addition of magnetic cell capture beads to said fluid processing reservoir.

In one embodiment of the system of the present invention one of said sealed fluid paths is for the selective addition of cell lysis buffer to said fluid processing reservoir.

In one embodiment of the system of the present invention said mixed cell suspension is whole blood.

In one embodiment of the system of the present invention said mixed cell suspension is whole blood and said cell lysis buffer is red blood cell (RBC) lysis buffer.

The system of the present invention finds use in a method for the isolation of a desired cell type from a mixed cell suspension. This method forms an additional aspect of the present invention. The embodiments presented herein for the features of the system of the present invention are equally applicable in connection with the method of the invention.

In one embodiment the method of the invention comprises the additional sequential steps following step (c) and before step (d) of:
  (i) adding a cell lysis reagent to said fluid processing reservoir wherein said cell lysis reagent lyses an undesired cell in said mixed cell suspension;
  (ii) circulating the contents of said fluid processing reservoir through the system such that said lysed undesired cell components are expelled and the remaining components are returned to said fluid processing reservoir; and,
  (iii) washing the remaining cells.

In one embodiment of the method of the invention said filter is a hollow fibre filter.

In one embodiment of the method of the invention said undesired cell components are expelled via said filter chamber column.

In one embodiment of the method of the invention said mixed cell suspension is whole blood.

In one embodiment of the method of the invention said cell lysis reagent lyses RBCs.

As a non-limiting example of the system of the present invention, a modified version of the existing Xuri Cell Harvester Processing Kit is envisaged, including additional connections for an additional process reagent (e.g. cell lysis buffer) and magnetic cell capture beads. The system can be achieved with only minimal alterations to the Xuri Cell Harvester system itself, including the addition of a magnet on a motorized arm to engage with the filter column. The adapted Xuri Cell Harvester could allow the system to isolate desired cell types from a mixed cell suspension, eliminating the current need for isolation by centrifugation using a SEPAX device. This would consolidate customer workflow and reduce the overall footprint of a cell therapy process. Additionally, the positive/negative selection agents could be purchased separately so they can be stored appropriately and can be added to a general Isolation Kit, offering a level of customisation. To ensure GMP quality, the components and their connection sites could have a seal similar to the READYMATE Connectors currently used in GE Life Sciences systems.

Such an exemplary embodiment is illustrated in the Figures herein.

Figure 6:
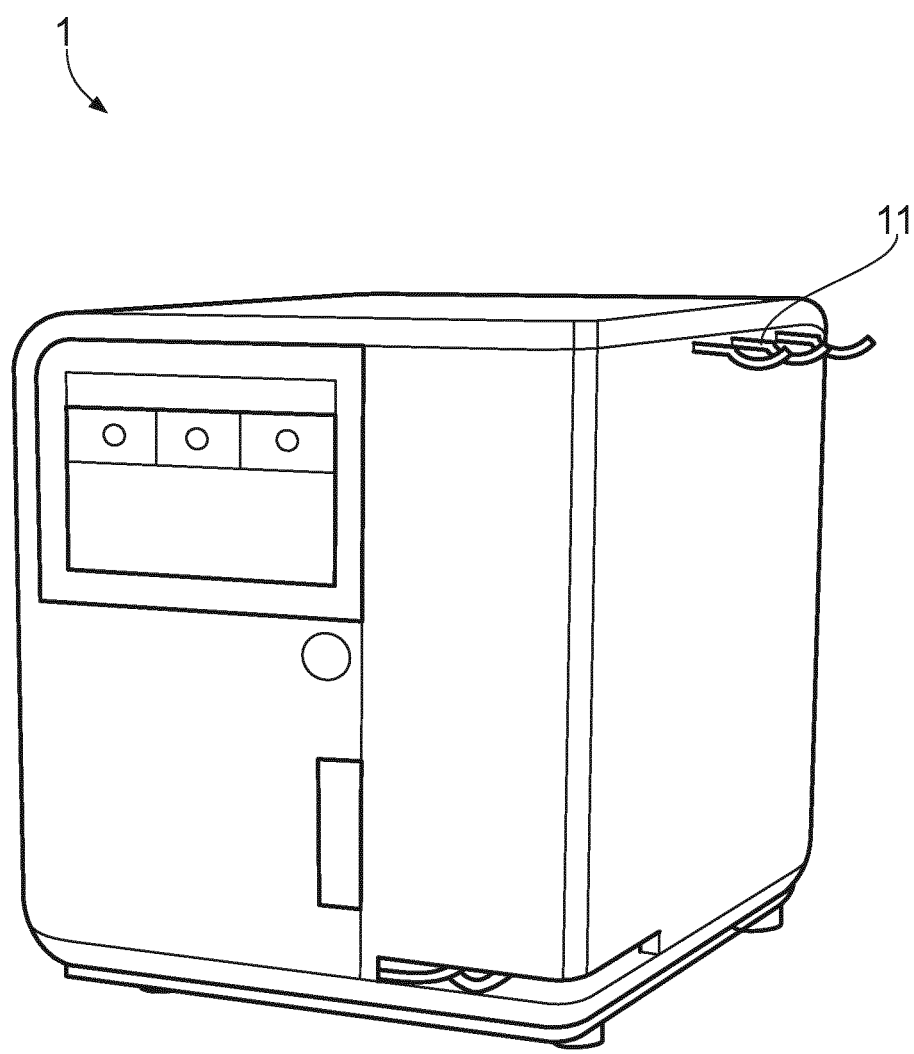
FIG. 6 shows an embodiment of the exterior of the system of the invention, including a hook (11) supported by the outside housing, which can be used for placement of a container of reagent such as the cell lysis reagent.
Figure 7:
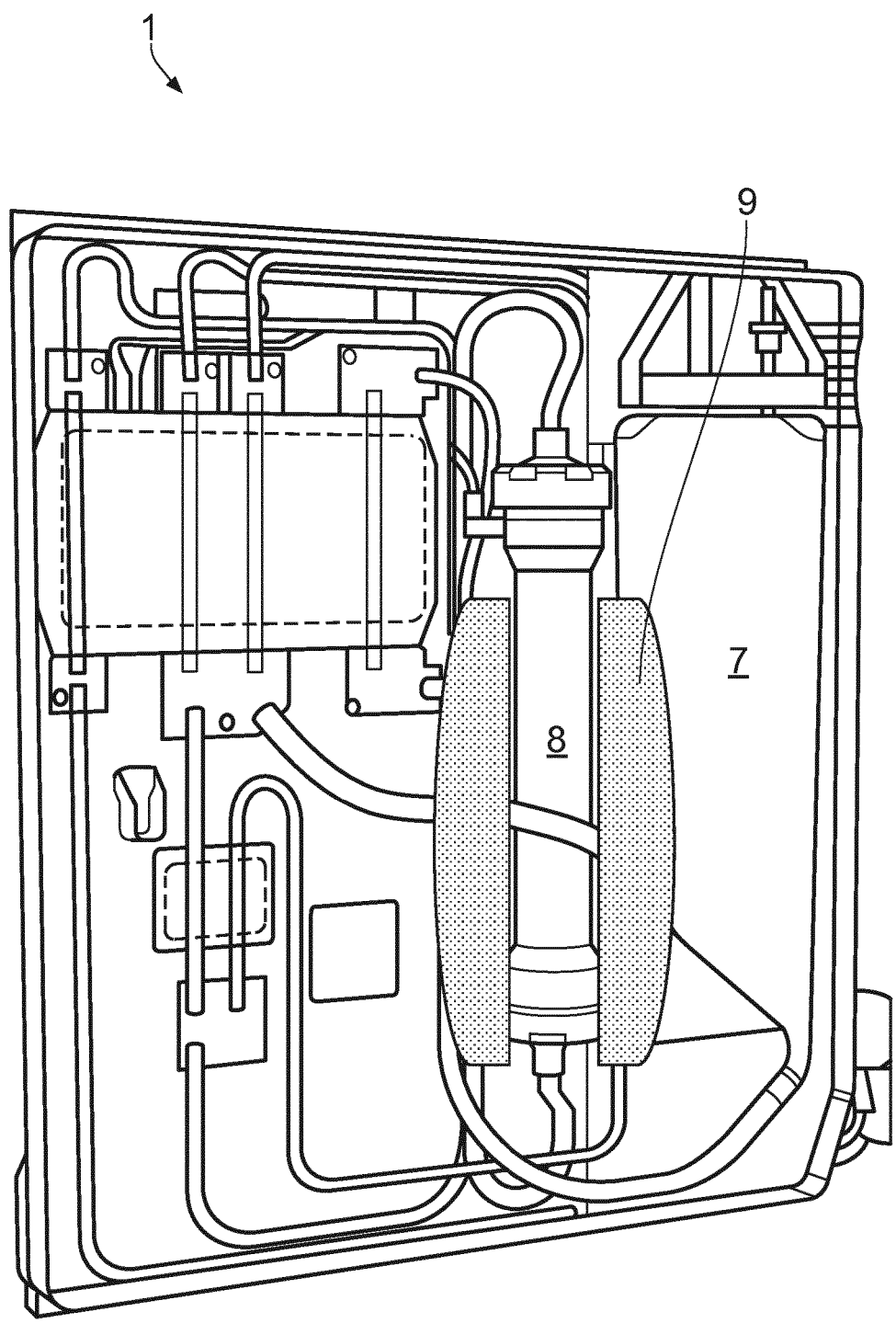
FIG. 7 illustrates an embodiment of the invention showing a similar embodiment to FIG. 6 with a cut out to show an embodiment of the internal configuration.
Figure 8:
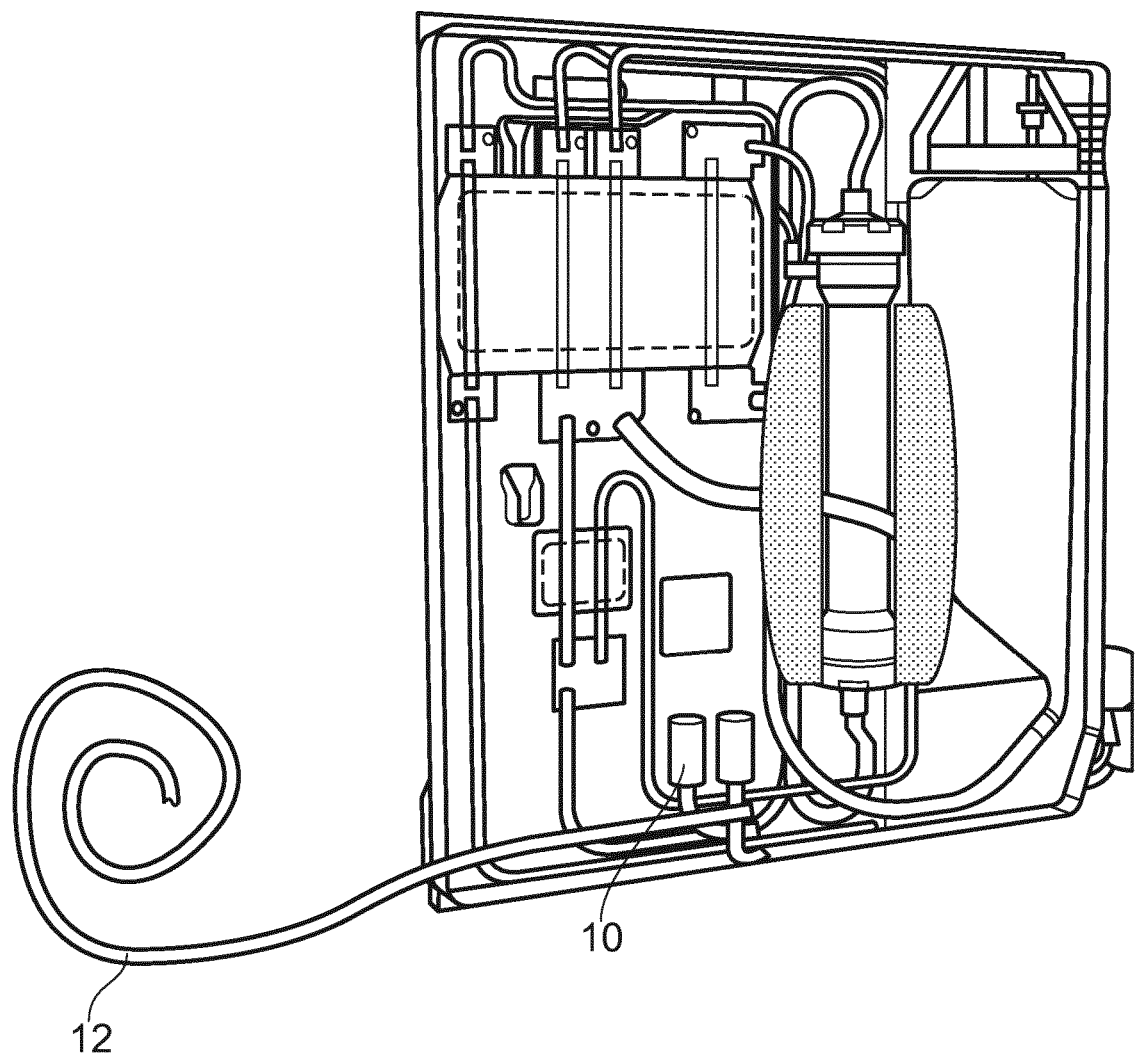
FIG. 8 shows an embodiment of the invention illustrating an example of how selection component slots can be arranged within the housing.
Figure 9:
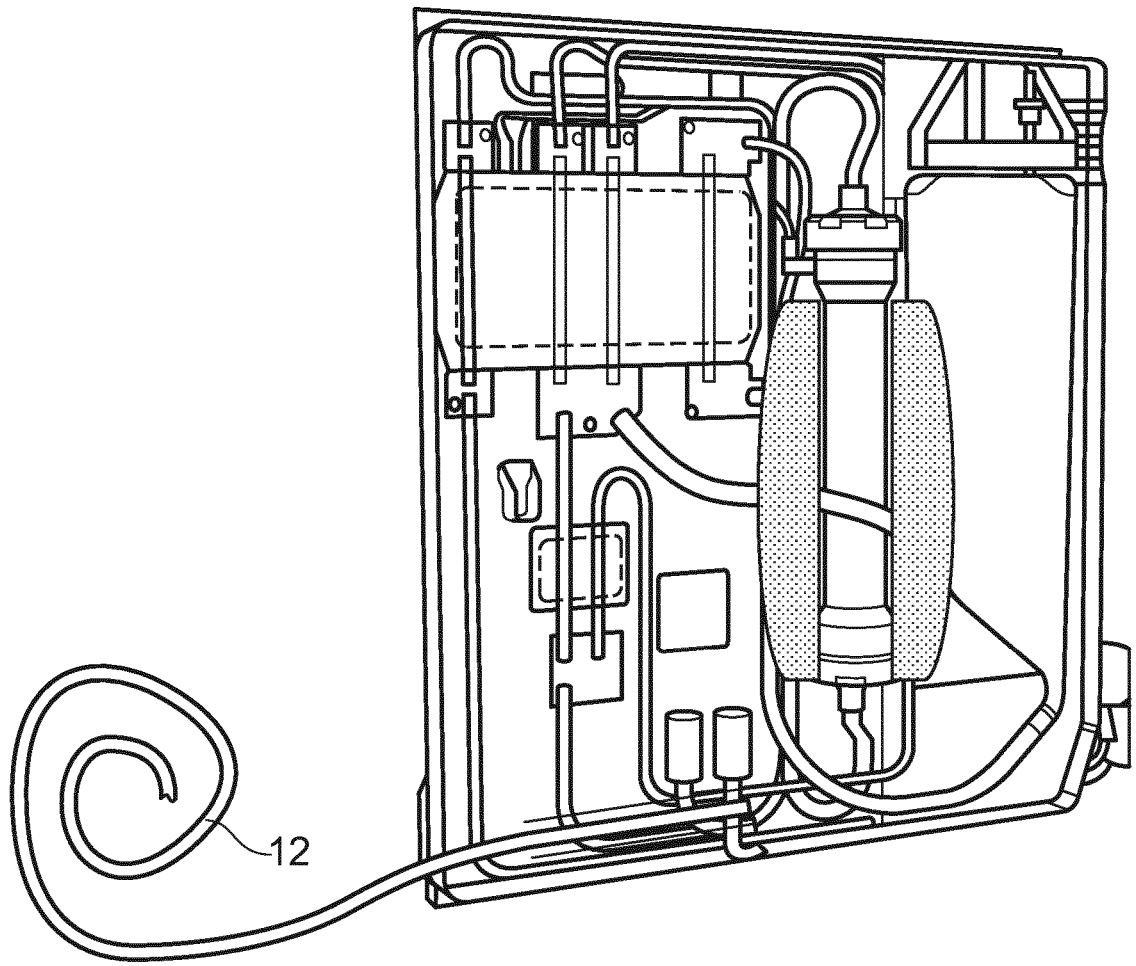
FIG. 9 shows the embodiment of FIG. 8 highlighting where an input line for additional reagent may be positioned.

The system detailed in FIGS. 1-5, is comprised of the Xuri Cell Harvester itself (1), the housing (2), and the following components mounted to the housing: the pump (3) which control what input material is added to the system, the sealed fluid paths (5) and the flexible tubes (6), the fluid processing reservoir (7), the filter (8), and the magnet (9). The selective capture beads (10) would be chosen by the user to be specific for the cells of interest by either positive or negative selection. A third hanging arm (11) seen in FIG. 6 is required as an update to the extant Xuri Cell Harvester (1) to hang the lysis buffer bag. An additional external line (12) seen in FIGS. 8 and 9 would also be required to attach to the lysis buffer bag.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. A system for harvesting and isolating cells from a mixed cell suspension wherein said system comprises a housing for accommodating the following functional elements:
  at least one fluid pump;
  at least one valve; and,
  a magnet;
  the system further comprising a fluidic arrangement including:

a fluid processing reservoir;

a filter suitable for separating cells from the mixed cell suspension; and a plurality of sealed fluid paths, wherein at least portions of the plurality of sealed fluid paths comprise flexible tubes providing fluid communication at least between the filter and the fluid processing reservoir, which are manipulatable by the at least one fluid pump, to provide fluid flow in one or more of the plurality of sealed fluid paths and/or by the at least one valve to restrict fluid flow in one or more of the plurality of sealed fluid paths;

wherein the magnet is arranged to selectively and directly engage with the filter when the filter is inserted into the housing; and wherein one or more of the plurality of sealed fluid paths, the fluid processing reservoir, and the filter are provided as a processing kit removably insertable into the housing, such that the processing kit is entirely disposed within the housing when inserted therein.

2. The system as defined in claim 1, wherein the at least one fluid pump, the at least one valve, and the magnet are present in the system.

3. The system as defined in claim 1, wherein the plurality of sealed fluid paths in the processing kit are arranged in a flat plane.

4. The system as defined in claim 1, wherein at least one of the plurality of sealed fluid paths is provided separately to the processing kit and fluidly connected to the fluid processing reservoir via selection component slots.

5. The system as defined in claim 1, wherein the magnet is present in the system on a motorized arm.

6. The system as defined in claim 1, wherein the filter is a hollow fibre filter.

7. The system as defined in claim 1, further comprising a weighing mechanism operable to weigh the fluid processing reservoir in use.

8. The system as defined in claim 1, wherein the at least one fluid pump or the at least one valve, in a retracted position, allow insertion and removal of the processing kit, and are driven into an operative position once the processing kit is inserted into the housing.

9. The system as defined in claim 1, wherein the housing includes a pair of guide rails to guide the processing kit into the housing during insertion, the pair of guide rails and the processing kit having complementary guiding formations including a stop feature.

10. The system as defined in claim 9, wherein the pair of guide rails are supported on an internal frame, wherein the internal frame also supports the remaining functional elements.

11. The system as defined in claim 10, wherein the at least one pump includes a peristaltic type pump head and the at least one valve is a pinch type valve including pinch fingers, and wherein the internal frame further supports reaction faces for reacting the forces exerted by the peristaltic type pump head and by the pinch fingers.

12. The system as defined in claim 11, wherein the internal frame comprises one or more through-apertures allowing the peristaltic type pump head and pinch fingers to access the flexible tubes from one side of the internal frame and allowing the reaction faces to access the flexible tubes on an opposing side of the internal frame.

13. The system as defined in claim 1, wherein at least one of the plurality of sealed fluid paths is for the selective addition of magnetic cell capture beads to the fluid processing reservoir.

14. The system as defined in claim 1, wherein at least one of the plurality of sealed fluid paths is for the selective addition of cell lysis buffer to the fluid processing reservoir.

15. The system as defined in claim 1, wherein the mixed cell suspension is whole blood.

16. The system as defined in claim 14, wherein the mixed cell suspension is whole blood and the cell lysis buffer is red blood cell (RBC) lysis buffer.

17. A method to isolate a desired cell type from a mixed cell suspension wherein the method comprises the following sequential steps:
   a. providing the system as defined in claim 1;
   b. inserting and connecting the functional elements as defined in claim 1;
   c. adding the mixed cell suspension to the fluid processing reservoir;
   d. adding magnetic cell capture beads to the fluid processing reservoir wherein the magnetic capture beads selectively bind either to a specific undesired cell type or to a specific desired cell type; and
   e. engaging the magnet with the filter to either trap the undesired cell type and allow the desired cell type to return to the fluid processing reservoir, or to trap the desired cell type in the filter and allow the undesired cell type to flush to waste.

18. The method as defined in claim 17 which further comprises additional sequential steps following step (c) and before step (d) of:
   (i) adding a cell lysis reagent to the fluid processing reservoir wherein the cell lysis reagent lyses an undesired cell in the mixed cell suspension;
   (ii) circulating contents of the fluid processing reservoir through the system such that the lysed undesired cells are expelled and remaining cells are returned to the fluid processing reservoir; and,
   (iii) washing the remaining cells.

19. The method as defined in claim 18, wherein the filter is a hollow fibre filter.

20. The method as defined in claim 19, wherein the undesired cells are expelled via a filter chamber column.

21. The method as defined in claim 17, wherein the mixed cell suspension is whole blood.

22. The method as defined in claim 18, wherein cell lysis reagent lyses RBCs.

23. The system as defined in claim 1, wherein the magnet is disposed along a length of the filter when the magnet is engaged with the filter.

* * * * *